United States Patent [19]

Boudjouk et al.

[11] Patent Number: 5,550,269
[45] Date of Patent: Aug. 27, 1996

[54] METHOD FOR REDISTRIBUTION OF TRICHLOROSILANE

[75] Inventors: Philip Boudjouk, Fargo, N. Dak.;
Steven D. Kloos, Chanhassen, Minn.

[73] Assignee: North Dakota State University Research Foundation, Fargo, N. Dak.

[21] Appl. No.: 560,456

[22] Filed: Nov. 17, 1995

[51] Int. Cl.$^6$ .................... C07F 7/10; C07F 7/08
[52] U.S. Cl. .................. 512/415; 556/424; 556/469; 556/480; 423/342
[58] Field of Search .................. 512/415, 469, 512/480, 424; 423/342

[56] References Cited

U.S. PATENT DOCUMENTS

| | | | |
|---|---|---|---|
| 2,834,648 | 5/1958 | Bailey et al. | 423/342 |
| 3,044,845 | 7/1962 | Whitehead | 23/14 |
| 3,147,071 | 9/1964 | Jenkner | 556/469 X R |
| 4,038,371 | 7/1977 | Marin | 423/342 |
| 4,395,389 | 7/1983 | Seth | 423/342 X R |
| 4,613,491 | 9/1986 | Jung et al. | 423/342 X R |
| 4,746,752 | 5/1988 | Lepage | 556/469 |
| 5,026,533 | 6/1991 | Matthes et al. | 423/342 |

*Primary Examiner*—Paul F. Shaver
*Attorney, Agent, or Firm*—William F. Boley

[57] ABSTRACT

A method for the redistribution of trichlorosilane in the presence of N,N,N',N'-tetraethylethylenediamine (TEEDA) to form a complex comprising dichlorosilane and TEEDA. The dichlorosilane can be disassociated from the TEEDA by a means such as heating and then used in standard processes requiring dichlorosilane. Alternatively, the complex comprising the dichlorosilane and TEEDA can be used as a reactant for hydrosilation of $\alpha,\beta$-unsaturated olefinic nitriles or reacted with Grignard type reagents to make organosilanes.

18 Claims, No Drawings

METHOD FOR REDISTRIBUTION OF TRICHLOROSILANE

BACKGROUND OF INVENTION

The present invention is a method for the redistribution of trichlorosilane in the presence of N,N,N',N'-tetraethylethylenediamine (TEEDA) to form a complex comprising dichlorosilane and TEEDA. The dichlorosilane can be disassociated from the TEEDA by a means such as heating and then used in standard processes requiring dichlorosilane. Alternatively, the complex comprising the dichlorosilane and TEEDA can be used as a reactant for hydrosilation of $\alpha,\beta$-unsaturated olefinic nitriles or reacted with Grignard type reagents to make organosilanes.

Typical processes for producing chlorosilanes, such as the reaction of hydrogen chloride with particulate silicon, result in a product that is primarily trichlorosilane. The ability to redistribute trichlorosilane to dichlorosilane can provide flexibility in meeting the demand for each of these chlorosilanes. Under typical uncatalyzed conditions the redistribution of trichlorosilane results in only about a 15 mole percent redistribution of trichlorosilane to dichlorosilane. The present method can provide for essentially a 100 mole percent redistribution of trichlorosilane to dichlorosilane. Therefore, the present method provides a more efficient method for redistribution of trichlorosilane to dichlorosilane. Furthermore, the present method provides a complex comprising dichlorosilane and TEEDA that is a solid and can be more easily and safely handled than dichlorosilane, which, under ambient conditions is a gas.

It is known that certain nitrogen containing compounds can catalyze the redistribution of chorohydrogen silanes. For example, Jex et al., U.S. Pat. No. 3,044,845, teach that dichlorosilane can be produced from trichlorosilane by forming a mixture of trichlorosilane, hexamethyltriaminotriazine or pyridine or a hydrocarbon-substituted pyridine as a catalyst and, as a promoter for the catalyst, a liquid halohydrocarbon in which trichlorosilane is soluble and heating the mixture.

Marin, U.S. Pat. No. 4,038,371, teaches that trichlorosilane is redistributed to dichlorosilane in the presence of a tetraalkylurea as a catalyst.

Lepage et al., U.S. Pat. No. 4,746,752, teach that silanes can be redistributed in the presence of a catalyst comprising (i) a quaternary ammonium salt or quaternary phosphonium salt, (ii) a tertiary amine, or (iii) an ion-exchange resin comprising tertiary amine or quaternary ammonium groups.

Matthes et al., U.S. Pat. No. 5,026,533, teach that an alkylamino trialkoxysilane chemically bound on a support is catalytic for the redistribution of trichlorosilane to dichlorosilane.

The cited art does not recognize that N,N,N',N'-tetraethylethylenediamine (TEEDA) can redistribute trichlorosilane to form a complex comprising dichlorosilane and the TEEDA.

SUMMARY OF INVENTION

The present invention is a method for the redistribution of trichlorosilane in the presence of N,N,N',N'-tetraethylethylenediamine (TEEDA) to form a complex comprising dichlorosilane and TEEDA. The dichlorosilane can be disassociated from the TEEDA by a means such as heating and then used in standard processes requiring dichlorosilane. Alternatively, the complex comprising the dichlorosilane and TEEDA can be used as a reactant for hydrosilation of $\alpha,\beta$-unsaturated olefinic nitriles or reacted with Grignard type reagents to make organosilanes.

DESCRIPTION OF INVENTION

The present invention is a method for the redistribution of trichlorosilane. The method comprising:

(A) contacting trichlorosilane with N,N,N'N'-tetraethylethylenediamine forming a complex comprising dichlorosilane and N,N,N',N'-tetraethylethylenediamine and (B) recovering the complex comprising dichlorosilane and N,N,N',N'-tetraethylethylenediamine.

Also, formed as a redistribution product of the present method is tetrachlorosilane. The tetrachlorosilane can be recovered by standard methods such as distillation and used in standard processes requiring tetrachlorosilane.

Although the present method may be run in the gas phase, it is preferred that the method be run in a liquid phase. The trichlorosilane can be contacted with the N,N,N',N'-tetraethylethylenediamine (TEEDA) in any standard reactor suitable for contacting a chlorosilane in mixture with a second reactant. The reactor can be, for example, a continuous-stirred batch type or semi-batch type reactor or a continuous-type reactor.

It is preferred that the present method be run under essentially anhydrous conditions. Therefore, it is useful to purge the reactor with a dry inert gas such as nitrogen and to maintain a blanket of such gas in the reactor.

The mole ratio of trichlorosilane to TEEDA is not critical to the present invention and can be varied within wide limits. Generally a trichlorosilane to TEEDA mole ratio within a range of about 0.1:1 to 10:1 is considered useful. Preferred is when the mole ratio of trichlorosilane to TEEDA is greater than about stoichiometric. Even more preferred is when the mole ratio of trichlorosilane to TEEDA is within a range of about 2:1 to 5:1.

It is preferred that the method be run in the presence of an organic solvent as a diluent. Any organic solvent which does not interfere with the redistribution of the trichlorosilane and formation of the complex comprising dichlorosilane and TEEDA may be used. It is preferred that the contact of the trichlorosilane with the TEEDA be effected in the presence of an organic solvent in which the complex comprising dichlorosilane and TEEDA is soluble. Examples of organic solvents useful as a diluent in the present method include dichloromethane and 1,2-dichloroethane. The preferred polar organic solvent used as a diluent is dichloromethane. The volume of the organic solvent used as a diluent in the present method can be within a range comprising no solvent to greater than two times the combined total volume of the trichlorosilane and TEEDA. Preferred is when the volume of organic solvent used as diluent is within a range of about 0.3 volume to an equal volume of the combined total volume of the trichlorosilane and TEEDA.

A complex comprising dichlorosilane and TEEDA is recovered from the method. Recovery of the complex can consist of simply storing the reaction product as made. The complex has limited stability at room temperature and when exposed to air. However, in the absence of air and at lower temperatures the complex can be stable for several weeks. In a preferred process after contact of the trichlorosilane with the TEEDA, in the presence or absence of the solubilizing organic solvent, a second organic solvent is added to effect precipitation of the complex comprising dichlorosilane and TEEDA from solution. Any organic solvent which effects precipitation of the complex comprising dichlorosilane and TEEDA from solution and does not react with the complex may be used in the present method. Useful organic solvents for precipitation of the complex include, for example, pentane, hexane, and tetrahydrofuran. A preferred organic solvent for precipitating the complex is pentane.

In a preferred method, the trichlorosilane is contacted with the TEEDA at a molar ratio of trichlorosilane to TEEDA in a range of about 2:1 to 5:1 in the presence of a diluent organic solvent such as dichloromethane and then the complex of dichlorosilane and TEEDA is precipitated from solution by the addition of a second organic solvent such as pentane.

The present method may be run within a temperature range of about 0° C. to the boiling point of trichlorosilane. Preferred is when the method is run within a temperature range of about 15° C. to 30° C.

The complex comprising dichlorosilane and TEEDA prepared by the present method may be dissociated by heating to recover the dichlorosilane from the complex. The dichlorosilane may then be used in standard reactions and processes requiring dichlorosilane as a feed material or reactant.

The complex comprising dichlorosilane and TEEDA prepared by the present method can be reacted with Grignard type reagents of the general formula RMgCl, where R is an alkyl or aryl radical. The radical R can be for example methyl, ethyl, propyl, tert-butyl, or phenyl. The reaction of the complex comprising dichlorosilane and TEEDA with Grignard type reagents can be conducted by standard methods known in the art for reacting chlorosilanes with Grignard type reagents.

The complex comprising dichlorosilane and TEEDA can be reacted with α,β-unsaturated olefinic nitriles described by formula

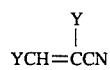

to form cyanoalkylsilanes, where each Y is independently selected from a group consisting of hydrogen and lower alkyl radicals comprising one to eight carbon atoms. The unsaturated olefinic nitrile can be, for example, acrylonitrile, methacrylonitrile, crotononitrile, ethylacrylonitrile, 1-cyanobutene-1, or 2-cyanooctene-1. The complex comprising dichlorosilane and TEEDA may be reacted with the α,β-unsaturated olefinic nitrile to form a cyanoalkylsilane at a temperature within a range of about 0° C. up to the dissociation temperature of the complex comprising dichlorosilane and TEEDA. Preferred is when the reaction is run at a temperature within a range of about 20° C. to 50° C.

The following examples are provided to illustrate the present invention. These examples are not intended to limit the scope of the claims herein.

EXAMPLE 1

The ability of trichlorosilane to redistribute in the presence of tetraethylethylenediamine (TEEDA) and methylene chloride to form a complex comprising dichlorosilane and TEEDA was evaluated. All reactions were performed in a glass flask under a blanket of dry nitrogen. Trichlorosilane was distilled before use. TEEDA was dried by refluxing over $CaH_2$ and then distilled. Dichloromethane was distilled from $P_2O_5$ just prior to use. The volumes of materials placed in the flask are provided in Table 1. Materials were added to the flask through a rubber septum by means of a syringe.

The dichloromethane was added to the flask first, followed by addition of trichlorosilane. TEEDA was then added to the flask and the content of the flask allowed to cool to room temperature. The volumes of trichlorosilane, TEEDA, and dichloromethane added to the flask are described in Table 1. Pentane was then added to the flask and the flask and its content stored at −20° C. for 16 hours. The volume of pentane added to the flask is described in Table 1. A crystalline precipitate formed during addition of the pentane. After 16 hours the liquid was removed from the precipitate. The precipitate was found to have a melting point of 101°–102° C. The precipitate was determined to be a complex of dichlorosilane and TEEDA by $^1H$ NMR δ 4.99 (s, 2H, SiH), δ 2.91 (q, 8H, J=7.2 Hz, $CH_2CH_3$), δ 2.78 (s, 4H, $CH_2CH_2$), δ 1.13 (t, 12H, J=7.2, $CH_3$ ); $^{13}C$ NMR 48.5(br,$CH_2CH_3$),47.57 (m,$CH_2CH_2$),10.0 (b, $CH_2CH_3$);$^{29}Si$ NMR(−30° C.),δ −120.2 (d,$^JSiH$=404 $H_3$).

The percent yield of the complex comprising dichlorosilane and TEEDA is presented in Table 1 as a percent of the added TEEDA complexed with dichlorosilane.

The complex comprising the dichlorosilane and TEEDA was determined by X-ray analysis to be a hexacoordinate adduct of dichlorosilane with both nitrogen atoms of the TEEDA chelating silicon. The complex comprising dichlorosilane and TEEDA was found to be stable under nitrogen for at least two months at room temperature, soluble in dichloromethane and 1,2-dichloroethane, slightly soluble in tetrahydrofuran, and virtually insoluble in pentane and hexane.

TABLE 1

Redistribution of Trichlorosilane in The Presence of TEEDA to Form a Complex Comprising Dichlorosilane and TEEDA

| $HSiCl_3$ | | TEEDA | | $HSiCl_3$:TEEDA | $CH_2Cl_2$ | Pentane | Yield |
|---|---|---|---|---|---|---|---|
| mL | mmol | mL | mmol | Molar Ratio | mL | mL | % |
| 2.4 | 23.4 | 05.0 | 23.4 | 1:1 | 15 | 16 | 17 |
| 0.8 | 8.0 | 1.7 | 8.0 | 1:1 | 5 | 10 | 26 |
| 4.7 | 46.9 | 5.0 | 23.4 | 2:1 | 15 | 25 | 50 |
| 28.4 | 281 | 20.0 | 93.8 | 3:1 | 50 | 100 | 86 |
| 37.9 | 375 | 20.0 | 93.8 | 4:1 | 50 | 100 | 98 |
| 17.0 | 169 | 9.0 | 42.2 | 4:1 | 20 | 20 | 90 |
| 9.5 | 93.8 | 3.5 | 16.4 | 5.7:1 | 10 | 30 | 94 |

EXAMPLE 2

The ability of a complex comprising dichlorosilane and TEEDA to hydrosilate acrylonitrile was evaluated. In a drybox, 0.750 g of a complex comprising dichlorosilane and TEEDA, prepared as described in Example 1, was placed in a 10 mL single-neck flask. The flask neck was fitted with a rubber septum and the flask removed from the drybox. Dichloromethane (4.0 mL) was added to the flask to dissolve the complex comprising dichlorosilane and TEEDA, followed by addition of 0.181 mL of acrylonitrile. The reaction mixture was stirred at room temperature and samples withdrawn for analysis by NMR at the times described in Table 2. Percent yield (% Yield) was calculated by integrating the acrylonitrile signal versus the product peaks. The column labelled "% conversion" provides the percent of acrylonitrile converted to product. In Table 2 product A is $Cl_3SiCH_2CH_2CN$, product B is $Cl_2HSiCH_2CH_2CN$, and product C is $ClH_2SiCH_2CH_2CN$.

TABLE 2

Hydrosilation of Acrylonitrile by a Complex Comprising Dichlorosilane and TEEDA

| Time (Days) | % Yield | | | % Conversion |
|---|---|---|---|---|
| | A | B | C | |
| 1 | 12 | 37 | 14 | 63 |
| 2 | 9 | 39 | 37 | 85 |
| 3 | 6 | 41 | 43 | 90 |
| 4 | 6 | 34 | 51 | 91 |

EXAMPLE 3

The ability of a complex comprising dichlorosilane and TEEDA to react with PhMgCl was evaluated. In a drybox, 3 g of a complex comprising dichlorosilane and TEEDA prepared as described in Example 1 was placed in a 250 mL two-neck flask. The flask was removed from the drybox and fitted with a stirbar, condenser, and rubber septum. Then 10 ml of $CH_2Cl_{12}$ and 30 mL of tetrahydrofuran were added to the flask through the septum. A Grignard type reagent comprising 13.2 mL of PhMgCl (Ph=phenyl) was added to the flask over five minutes. The reaction was stirred overnight and then the solvents removed by evaporation. Ether (30 mL) was added to dissolve the product, followed by HCl (80 mL) to destroy unreacted starting materials and form water-soluble TEEDA.2HCl. The resulting liquid mixture was extracted with ether and the extract distilled to yield 1.51 g of $Ph_2SiH_2$ as determined by $^1H$ NMR and $^{29}Si$ NMR.

EXAMPLE 4

Isolation of tetrachlorosilane from the reaction of trichlorosilane with TEEDA. A mixture was formed consisting of 20 mL of dichloromethane and 11.4 mL of trichlorosilane in a 100 mL one-neck flask. Then, 6.0 mL of TEEDA was added to the flask. Pentane (20 mL) was added to the flask causing the formation of a crystalline precipitate. After storage at −20° C. for 16 h, 5.7 g of precipitate was isolated and determined to be a complex comprising dichlorosilane and TEEDA by methods described in Example 1. Volatiles were distilled from the liquid removed from the reaction flask. Pentane, $CH_2Cl_2$, and $HSiCl_3$ were distilled from the collected volatiles leaving 5.56 g of a residual liquid. $^1H$ NMR and $^{29}Si$ NMR of the residual liquid showed that it contained approximately a 103:38:1 molar ratio of $SiCl_4$:$CH_2Cl_2$:pentane.

We claim:

1. A method for redistribution of trichlorosilane, the method comprising:
   (A) contacting trichlorosilane with N,N,N'N'-tetraethylethylenediamine forming a complex comprising dichlorosilane and N,N,N',N'-tetraethylethylenediamine and
   (B) recovering the complex comprising dichlorosilane and N,N,N',N'-tetraethylethylenediamine.

2. A method according to claim 1, where the method is conducted in liquid phase.

3. A method according to claim 1, where the mole ratio of trichlorosilane to N,N,N',N'-tetraethylethylenediamine added to the method is within a range of about 0.1:1 to 10:1.

4. A method according to claim 1, where the mole ratio of trichlorosilane to N,N,N',N'-tetraethylethylenediamine added to the method is within a range of about 2:1 to 5:1.

5. A method according to claim 2, where the trichlorosilane is contacted with the N,N,N',N'-tetraethylethylenediamine in the presence of an organic solvent in which the resulting complex is soluble.

6. A method according to claim 5, were the organic solvent is selected from a group consisting of dichloromethane and 1,2-dichloroethane.

7. A method according to claim 5, where the organic solvent is dichloromethane.

8. A method according to claim 5, where the volume of organic solvent added to the method is within a range of about 0.3 volume to an equal volume of the combined total volume of the trichlorosilane and N,N,N',N'-tetraethylethylenediamine.

9. A method according to claim 2, where recovery of the complex comprising dichlorosilane and N,N,N',N'-tetraethylethylenediamine is effected by precipitation with an organic solvent which effects precipitation of the complex.

10. A method according to claim 9, where the organic solvent is selected from a group consisting of hexane, pentane, and tetrahydrofuran.

11. A method according to claim 9, where the organic solvent is pentane.

12. A method according to claim 2, where the trichlorosilane is contacted with the N,N,N',N'-tetraethylethylenediamine at a mole ratio in a range of about 2:1 to 5:1 in the presence of an organic solvent in which the resulting complex is soluble and recovery of the complex is effected by the addition of an organic solvent which effects precipitation of the complex.

13. A method according to claim 1, where the trichlorosilane is contacted with the N,N,N',N'-tetraethylethylenediamine at a temperature within a range of about 15° C to 30° C.

14. A composition comprising dichlorosilane and N,N,N',N'-tetraethylethylenediamine prepared by the process of claim 1.

15. A composition comprising a complex of dichlorosilane and N,N,N',N'-tetraethylethylenediamine.

16. A method of forming an organosilane, the method comprising contacting a complex comprising dichlorosilane and N,N,N',N'-tetraethylethylenediamine with a reagent described by formula RMgCl, where R is an alkyl or aryl radical.

17. A method of forming a cyanoalkylsilane, the method comprising contacting a complex comprising dichlorosilane and N,N,N',N'-tetraethylethylenediamine with an α,β-unsaturated olefinic nitrile described by formula YCH=C(Y) CN, where each Y is independently selected from a group consisting of hydrogen and lower alkyl radicals comprising one to eight carbon atoms.

18. A method according to claim 17, where the unsaturated olefinic nitrile is selected from a group consisting of acrylonitrile, methacrylonitrile, crotononitrile, ethylacrylonitrile, 1-cyanobutene-1, and 2-cyanooctene-1.

* * * * *